United States Patent [19]

Chu et al.

[11] Patent Number: 4,686,312

[45] Date of Patent: Aug. 11, 1987

[54] AROMATICS PRODUCTION

[75] Inventors: Yung-Feng Chu; Arthur W. Chester, both of Cherry Hill, N.J.

[73] Assignee: Mobil Oil Corporation, New York, N.Y.

[21] Appl. No.: 922,230

[22] Filed: Oct. 23, 1986

Related U.S. Application Data

[63] Continuation-in-part of Ser. No. 577,721, Feb. 6, 1984, abandoned, which is a continuation of Ser. No. 333,844, Dec. 23, 1981, abandoned.

[51] Int. Cl.$^4$ .............................................. C07C 1/20
[52] U.S. Cl. .................................... 585/315; 585/312; 585/314; 585/408; 585/415; 585/469; 585/640
[58] Field of Search ............... 585/312, 315, 316, 408, 585/415, 469, 640, 314

[56] References Cited

U.S. PATENT DOCUMENTS

| | | | |
|---|---|---|---|
| 4,058,576 | 11/1977 | Chang et al. | 585/415 |
| 4,180,689 | 12/1979 | Davies et al. | 585/415 |
| 4,245,130 | 6/1981 | Jones et al. | 585/475 |
| 4,276,437 | 6/1981 | Chu | 585/475 |
| 4,334,114 | 6/1982 | Ellis | 585/415 |
| 4,392,989 | 7/1983 | Chu et al. | 585/415 |
| 4,544,788 | 10/1985 | Daviduk et al. | 585/501 |
| 4,547,612 | 10/1985 | Tabak | 585/533 |
| 4,642,402 | 2/1987 | Jensen | 585/415 |

Primary Examiner—Asok Pal
Attorney, Agent, or Firm—Alexander J. McKillop; Michael G. Gilman; L. G. Wise

[57] ABSTRACT

Disclosed is a multistage process for converting lower aliphatic oxygeanated hydrocarbon feedstock to hydrocarbon product rich in benzene, toluene and/or xylene which comprises:

contacting said oxygenated hydrocarbons in a primary stage with a medium pore shape selective acidic zeolite to an intermediate hydrocarbon product comprising predominantly aliphatic hydrocarbons;

contacting at least a portion of the aliphatic hydrocarbons from the primary stage with a secondary stage catalyst comprising gallium-promoted medium pore shape selective zeolite characterized by a constraint index within the approximate range of 1 to 12 and a silica to alumina ratio of about 20 to 100:1; thereby producing benzene, toluene and/or xylene.

10 Claims, 1 Drawing Figure

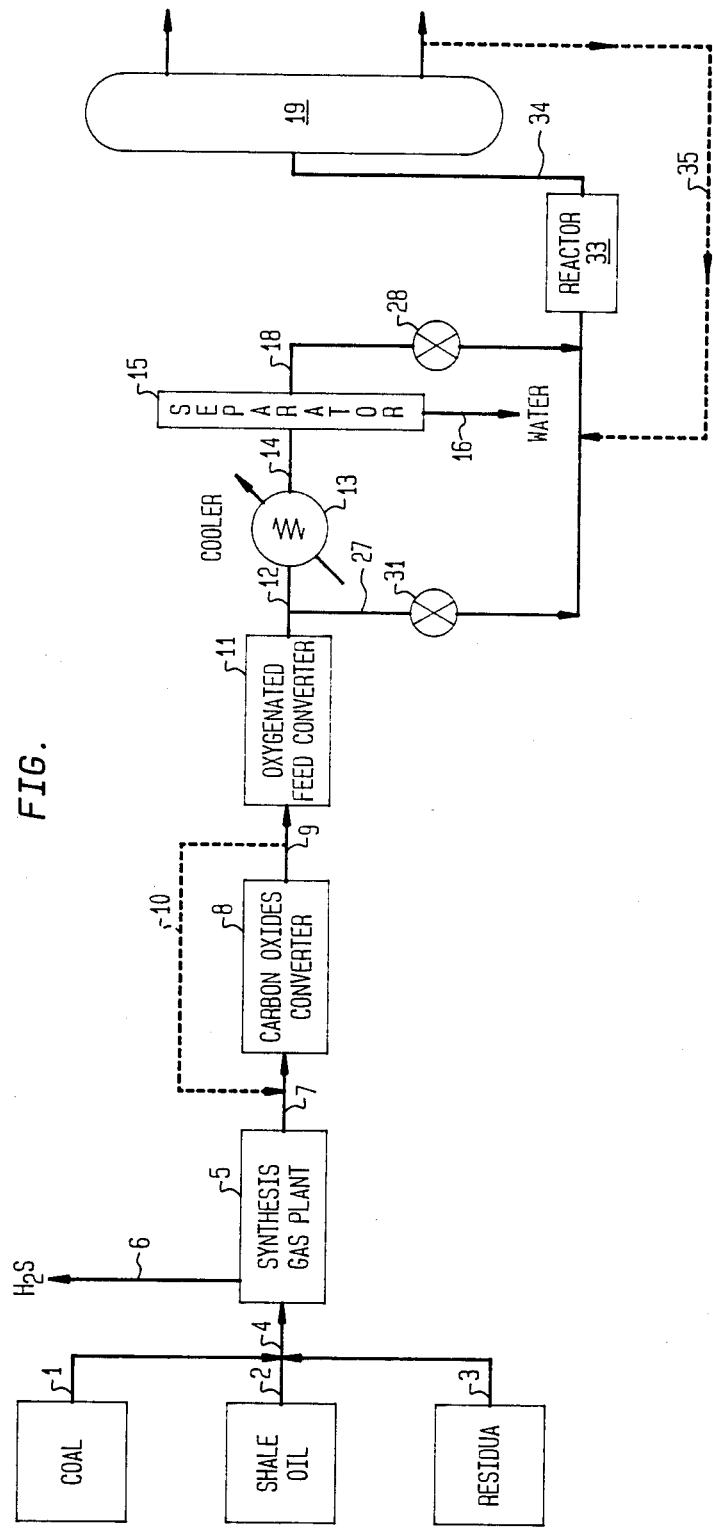

AROMATICS PRODUCTION

CROSS-REFERENCE TO RELATED APPLICATIONS

This is a continuation-in-part of application Ser. No. 577,721 filed Feb. 6, 1984, now abandoned, which is a continuation of application Ser. No. 333,844, filed Dec. 23, 1981, now abandoned.

NATURE OF INVENTION

This invention relates to processes and operating techniques for converting alcohols, aliphatic ethers, and industrial feedstreams containing these and other oxygenated lower aliphatic hydrocarbon compounds to lower aromatics compounds, such as benzene, toluene, xylenes, and other aromatics boiling within the range of gasoline. More specifically, this invention is concerned with increasing the conversion of $C_1$–$C_4$ oxygenates to predominantly $C_6$–$C_8$ benzenoids utilizing zeolite catalysts enhanced with metallic components such as gallium.

BACKGROUND OF THE INVENTION

Benzene, toluene, and xylenes (BTX) are basic building blocks of modern petrochemical industries. The present source of these compounds primarily is the refining of petroleum. As petroleum supplies dwindle so does the supply of benzene, toluene and xylene. Alternative sources must be developed for these compounds. We have discovered a process for making benzene, toluene and xylene which utilizes materials which can be indirectly derived from a readily available source, synthesis gas.

Development of fossil fuel conversion processes has enabled the production of oxygenated hydrocarbons from coal, natural gas, shale oil, etc. Synthesis gas ($CO+H_2$) is readily obtained from the fossil fuels and can be further converted to lower aliphtic oxygenates, especially methanol (MeOH) and/or dimethyl ether (DME). U.S. Pat. No. 4,237,063 (Bell et al) discloses the conversion of synthesis gas to oxygenated hydrocarbons using metal cyanide complexes. U.S. Pat. No. 4,011,275 (Zahner) discloses the conversion of synthesis gas to methanol and dimethyl ether by passing the mixture over a zinc-chromium acid or copper-zinc-alumina acid catalyst. U.S. Pat. No. 4,076,761 (Chang et al) discloses a process for making hydrocarbons from synthesis gas wherein an intermediate product formed is a mixture of methanol and dimethyl ether.

Processes for the conversion of coal and other hydrocarbons to a gaseous mixture comprising hydrogen and carbon monoxide, carbon dioxide, etc., are well known. Such a gaseous mixture hereinafter will be referred to simply as synthesis gas or syngas. An excellent summary of the art of gas manufacture, including synthesis gas, from solid and liquid fuels, is given in Encyclopedia of Chemical Technology, Edited by Kirk-Othmer, Second Edition, Volume 10, pages 353–433, (1966), Interscience Publsihers, New York, N.Y., the contents of which are herein incorporated by reference.

It has recently been demonstrated that alcohols, ethers, carbonyl and their analogous compounds may be converted to higher hydrocarbons, particularly aromatics-rich high octane gasoline, by catalytic conversion employing shape selective medium pore acidic zeolite catalyst, such as H-ZSM-5. This conversion is described in U.S. Pat. Nos. 3,894,103, '104, '106; 3,928,483, 3,907,915 (Chang et al ); which describe oxygenate conver sion techniques suitable for converting methanol or the like. The process has become known as the methanol-to-gasoline or "MTG" process, and produces mainly $C_5+$ gasoline range hydrocarbon products with $C_3$–$C_4$ LPG and $C_9+$ heavy aromatics. The desirable $C_6$–$C_8$ BTX can recovered as a separate product slate by conventional distillation and extraction techniques. These light aromatics are also produces in a related process for converting methanol to olefins (MTO), as described in U.S. Pat. No. 4,011,278 (Plank et al); 4,550,217 (Graziani et al); 4,513,160, 4,547,616 (Avidan et al), incorporated herein by reference.

An object of this invention is to increase the yield of products rich in benzene, toluene, and xylenes (i.e. greater than 50 percent aromatics) when oxygenated hydrocarbons such as methanol and dimethyl ether and product streams containing these and other oxygenated hydrocarbon compounds are converted to hydrocarbons rich in benzene, toluene and xylene. Another object of this invention is to improve present methods of converting readily available oxygenates to products rich in benzene, toluene and xylenes.

SUMMARY OF THE INVENTION

An improved process has been found for converting oxygenated hydrocarbon feedstock rich in methanol, dimethyl ether and/or other $C_1$–$C_4$ lower aliphatic oxygenates by contacting said feedstock at elevated temperature with an acid medium pore shape selective metallosilicate zeolite catalyst to produce heavier hydrocarbons containing predominanly aliphatics. This improvement comprises further converting at least a portion of the heavier hydrocarbons to light aromatics righ in benzene, toluene and/or xylene by contacting said heavier hydrocarbons at elevated temperature with a gallium metal-promoted medium pore shape selective metallosilicate zeolite catalyst under aromatization conditions to produce said light aromatics and $C_9+$ heavy aromatics. By recovering said $C_9+$ heavy aromatics for recycle and further conversion light aromatics production can be increased to give greater net yield of BTX. Preferrably, the metal-promoted zeolite catalyst comprises a ZSM-5 zeolite having deposited thereon about 0.1 to 1 wt % gallium metal promoter.

BRIEF DESCRIPTION OF THE DRAWING

The single FIGURE of the drawing is a process flow sheet depicting a typical conversion technique according to the present invention.

DESCRIPTION OF SPECIFIC EMBODIMENTS

Recent developments in zeolite technology have provided a group of medium pore siliceous materials having similar pore geometry to provide shape selective reaction sites. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The medium pore zeolites having Bronsted acid sites and a pore size of about 5 to 8 Angstroms may be utilized in the primary stage and secondary stage conversions. In the preferred embodiments, an aluminosilicate zeolite having a silica to alumina molar ratio of about 20 to 100:1 is preferred in both stages. This can provide an acid cracking (alpha) value of about 50 to 200 or more prior to any cation exchange of the zeolite. Aromatization and transalkylation reactions are promoted by a metal component, such as Pt, Pd, Zn, and especially Ga. In the primary stage reaction the acidic zeolite converts the oxygenate feedstock predominantly to aliphatic hydrocarbons, usually about 50 to 80 wt % olefins and paraffins, with a minor amount of aromatics being formed. In the secondary stage the hydrocarbon effluent from the primary stage is further converted to mainly aromatics, preferably at least 50% BTX employing a metal-promoted acidic zeolite of the ZSM-5 type.

The platinum, zinc or gallium in the catalyst composition used in the second stage can be present as the metal oxide and/or as metal ions if cations in the ZSM-5 type zeolite have been exchanged with the metal ions therein. In the case where the cations in the zeolite have been exchanged for metal ions, the metal ion is suitably provided as an aqueous solution of metal salts, such as, for instance, the soluble nitrate, chloride or sulfate salts of platinum, zinc or gallium. Such catalysts may be produced by conventional ion exchange techniques and the catalysts so produced by subsequently dried. For example, an aqueous solution of the metal compound such as tetramine platinum chloride, zinc chloride, or gallium nitrate may be placed in contact with zeolite at ambient or elevated temperature, e.g. by refluxing. The exchanged zeolite is then separated by decantation followed by filtration, washed several times with deionized water and finally dried. Before addition to the aqueous solution of the metal compound, the zeolite may be acid treated.

The process of the present invention may also be carried out using catalysts in which the platinum, zinc, or gallium is only impregnated on the surface of the zeolite or is incorporated in the intra-crystalline zeolite cavities as a metal compound which gives rise to a metal oxide during activation of the catalyst prior to contact with the hydrocarbon feedstock.

Where the catalyst composition is prepared by using a metal compound which ionizes in aqueous solution, for example, gallium nitrate, it is inevitable that some of the metal ions will be exchanged with the cations in the zeolite even if the preparation was directed to impregnation of the zeolite.

Whichever method of catalyst preparation is used, the amount of metal present in the catalyst compositions (metal plus zeolite) may vary for instance between 0.01 and 5 percent, preferably between 0.05 and 2 percent by weight. Obviously, a mixture of two or more metals can be incorporated into the zeolite by the methods discussed above. If zinc is present in the catalyst, it is preferred also to include palladium and gallium.

Medium pore zeolites exhibit constrained access and have a Constraint Index in the range of about 1 to 12. Typical medium pore shape selective metallosilicates include ZSM-5, ZSM-11, ZSM-22, ZSM-23, ZSM-35, ZSM-38 and ZSM-48. Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite. Other gallium-treated synthetic zeolites are disclosed in U.S. Pat. Nos. 4,175,057 and 4,180,689 (Davies).

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, gallium, zinc, palladium, calcium and/ or rare earth metals.

The drawing will now be used to illustrate this invention in certain of its aspects, without being limited thereto. Coal, shale oil, or residua, or a combination thereof, is conveyed via line 1, 2 and 3, respectively and thence via line 4 to the synthesis gas plant, 5, where it is converted to synthesis gas. If hydrogen sulfide is produced in this plant, it may be separated and sent via line 6 to a treatment plant (not shown) for sulfur recovery. Synthesis gas, previously treated in a catalytic carbon monoxide shift converter and then reduced in carbon dioxide content by selective sorption, is conveyed via line 7 to a first reaction zone 8, where it is at least partially converted catalytically to produce a carbon monoxide reduction product that contains at least 20% by weight of oxygenated products. Part or all of the unconverted synthesis gas may be separated from such reduction product and recycled via line 10.

That portion of reaction product not recycled through line 10 is conveyed to the reaction zone 11 where catalytic conversion to hydrocarbons and steam occurs. The reaction products from the second reaction zone 11 can then be diverted through line 27, valve 31 and conduit 29 to the reactor 33 where it is contracted with the ZSM-5 type metal promoted porous crystalline zeolite.

In the practice of this invention, the conversion in the reaction zone 11 is conducted at a temperature of about 250°–540° C. (500°–1000° F.), preferably about 300°–425° C. (600° to 800° F.), a pressure of subatmospheric to about 50 atmospheres, and at a liquid hourly space velocity of about 0.1 to 50 LHSV.

In one embodiment the reaction products in line 12 are conveyed via line 12 to a cooler, 13, and the cooled products are then conveyed via line 14 to a separator 15, which may be one integral unit. Gas is removed via line 17, and liquid hydrocarbon products via line 18. The liquid product , comprising at least 50% C4 to C9 aliphatics, is conveyed via line 18 to reactor 33 where it is contacted with the metal promoted zeolite, preferably Ga/ZSM-5, for conversion to aromatics rich in BTX.

Effluent from the reactor 33 is conveyed through line 35 optionally to a cooler and separator (not shown) and the liquid portion thereof is fractionated in a distillation tower 19 into fractions consisting of benzene, toluene and xylene. Any fraction containing hydrocarbons in excess of 9 carbon atoms can be recycled through reactor 33 for conversion by transalkylation, dealkylation and disproportionation to a product richer in benzene, toluene and xylene.

Preferably the ZSM-5 type zeolite has deposited thereon the equivalent in metal of between 0.1 and 5 percent by weight of zinc and between 0.01 and 1 percent of gallium of the total composition. In a typical, and preferred embodiment of the process of this invention, the feedstream of hydrocarbons is introduced into the reaction zone 33 at a temperature within the range of 315.6° C. (600° F.) and about 649° C. (1200° F.), a pressure within the range of $1.01 \times 10^5$ to $28.59 \times 10^5$ pascal (0 to 400 psig), and a WHSV of 0.1 to 10.

Preferred temperatures in the reaction zone 33 fall within the range of 426° C. (800° F.) to 566° C. (1050° F.) and preferred pressures fall within the range of $1.01 \times 10^5$ to $14.8 \times 10^5$ pascal (0 to 200 psig. A preferred weight hourly space velocity (WHSV) is between 0.2 and 3. These latter ranges of temperature, pressure and WHSV are believed to embody the best mode of conducting the process of this invention.

EXAMPLE 1

Acid or hydrogen-form ZSM-5 zeolite catalyst was impregnated with gallium, zinc or palladium, and platinum in the concentrations shown in Table 1. The catalyst was prepared in the form of extrudate in which the ratio of silica to alumina in the ZSM-5 was 70 to 1. A feedstock obtained from the treatment of synthesis gas with a carbon monoxide reducing catalyst after being first passed through a dehydration reactor and then further passed over a ZSM-5 catalyst zone corresponding to reaction zone 11 was then flowed over each catalyst at the conditions shown in Table 1. The results obtained show a substantial increase in the production of aromatics, namely benzenes, toluene and xylene.

In Tables II-V are shown the results obtained with the same feedstock and catalysts at different conditions of temperature and pressure. In Tables I-V the composition of the feed stock is shown in the column headed "Feed."

TABLE I

| Example No. | Feed | 1 | 2 | 3 | 4 | 5 |
|---|---|---|---|---|---|---|
| Catalyst | | HZSM-5 | Ga/HZSM-5 | Zn/Pd HZSM-5* | Pt/HZSM-5 | Ga/HZSM-5 |
| Metal Concentration, wt. % | | 0 | 0.5 | 2/1 | 0.1 | 0.5 |
| Temp., °C. (°F.) | | | | 537.8 (1000) | | |
| Pressure kPa, (psig) | | | | 101.4 (0) | | |
| WHSV | | | | 1 | | 0.5 |
| Conc. Benzene, Toluene and Xylene BTX, Wt % | 14.3 | 49.5 | 60.3 | 63.8 | 51.7 | 77.5 |
| Conc. of $C_9^+$ in Product, Wt % | 26.4 | 15.8 | 7.5 | 8.8 | 11.0 | 10.3 |
| $C_9^+$ Converted, Wt % | | 40.1 | 71.6 | 66.7 | 58.3 | 61.0 |

*40/1 mole ratio of $SiO_2$ to $Al_2O_3$ HZSM-5, all others 70/1 $SiO_2/Al_2O_3$

TABLE II

| Run No. | Feed | 1-1 | 1-2 | 1-3 |
|---|---|---|---|---|
| Catalyst | | | HZSM-5* | |
| Temperature, (°F.) °C. | (1000) 537.8 | (1050) 565.6 | (1100) 593.3 |
| Pressure: 101.4 kPa, (0 psig) | | | | |
| WHSV: 1 | | | | |
| Conc. of BTX in Prod. Wt. % | 14.3 | 49.5 | 55.6 | 58.7 |
| Prod. Distribution, Wt % $C_1-C_3$ | 1.3 | 32.8 | 30.5 | 21.8 |
| $C^4-C_9$ (non-aromatics) | 58.0 | 1.7 | 0.5 | 0.2 |
| Benzene | 11.0 | 16.5 | 18.1 | |
| Toluene | 2.7 | 23.0 | 25.7 | 26.9 |
| Xylenes | 11.4 | 15.5 | 13.4 | 13.7 |
| $C_9^+$ Aromatics | 19.6 | 9.6 | 9.0 | 7.8 |
| Durenes | 6.8 | 6.2 | 4.4 | 11.5 |
| Total | 100.0 | 100.0 | 100.0 | 100.0 |

*70/1 $SiO_2/Al_2O_3$ HZSM-5, no added metal.

TABLE III

| Run No. | Feed | 2-1 | 2-2 | 2-3 | 2-4 | 2-5 |
|---|---|---|---|---|---|---|
| Catalyst | | | | Ga/HZSM-5* | | |
| Temperature, °C. | | 537.8 | 532.8 | 565.6 | 510 | 510 |
| Temperature, °F. | | 1000 | 1000 | 1050 | 950 | 950 |
| Pressure: 101.4 kPa, (0 psig) | | | | | | |
| WHSV | | 1 | 0.5 | 1 | 1 | 0.5 |
| Conc. of BTX, Wt % | 14.3 | 60.3 | 77.5 | 59.6 | 51.2 | 72.7 |
| Product Distribution | | | | | | |
| $C_1-C_3$ | 1.3 | 31.0 | 11.7 | 23.7 | 32.8 | 16.2 |
| $C_4-C_9$ (non-aromatics) | 58.0 | 0.4 | 0.1 | 0.3 | 2.9 | 0.9 |
| BZ | 0.2 | 15.7 | 15.6 | 17.6 | 11.4 | 12.6 |
| Toluene | 2.7 | 28.9 | 39.6 | 27.5 | 24.6 | 36.2 |
| Xylenes | 11.4 | 15.7 | 21.7 | 14.5 | 15.2 | 23.9 |
| $C_9^+$ Aromatics | 19.6 | 5.8 | 5.4 | 11.2 | 7.8 | 7.2 |
| Durenes | 6.8 | 1.7 | 4.9 | 5.1 | 5.1 | 3.0 |

TABLE III-continued

| Run No. | Feed | 2-1 | 2-2 | 2-3 | 2-4 | 2-5 |
|---|---|---|---|---|---|---|
| Total | 100.0 | 99.2 | 99.6 | 100.0 | 100.0 | 100.0 |

*70/1 SiO$_2$/Al$_2$O$_3$ HZSM-5, containing 0.5 weight percent of gallium

TABLE IV

| Run No. | Feed | 3-1 | 3-2 | 3-3 | 3-4 |
|---|---|---|---|---|---|
| Catalyst | | Zn/Pd/HZSM-5* | | Zn/Pd/HZSM-5** | |
| Temperature, °C. | | 371.1 | 426.7 | 426.7 | 537.8 |
| Temperature, °F. | | 700 | 800 | 800 | 1000 |
| Pressure, 101.4 kPa, (0 psig) | | | | | |
| WHSV | | 1 | 1 | 3 | 1 |
| Conc. of BTX, Wt. % | 14.3 | 37.6 | 35.9 | 39.8 | 63.8 |
| Prod. Distribution Wt. % | | | | | |
| C$_1$-C$_3$ | 1.3 | 13.3 | 26.1 | 18.7 | 27.2 |
| C$_4$-C$_9$ (non-aromatics) | 58.0 | 26.1 | 14.2 | 19.0 | 0.1 |
| BZ | 0.2 | 2.7 | 3.6 | 3.0 | 18.8 |
| Toluene | 2.7 | 14.5 | 12.9 | 15.5 | 30.5 |
| Xylenes | 11.4 | 20.6 | 19.4 | 21.3 | 14.5 |
| C$_9$+ Aromatics | 19.6 | 14.6 | 15.1 | 12.4 | 5.9 |
| Durenes | 6.8 | 8.2 | 8.7 | 10.2 | 2.9 |
| Total | 100.0 | 100.0 | 100.0 | 100.1 | 99.9 |

*70/1 SiO$_2$/Al$_2$O$_3$ HZSM-5 containing 2 percent by weight of zinc and 1% by weight of palladium.
**40/1 SiO$_2$/Al$_2$O$_3$ HZSM-5 containing 2 percent by weight of zinc and 1% by weight of palladium.

TABLE V

| Run No. | Feed | 4-1 | 4-2 | 4-3 | 4-4 | 4-4 |
|---|---|---|---|---|---|---|
| Catalyst | | Pt/HZSM-5* | | | | |
| Temperature, °C. | | 371.1 | 426.7 | 482.2 | 537.8 | 565.6 |
| Temperature, °F. | | 700 | 800 | 900 | 1000 | 1050 |
| Pressure, 101.4 kPa (0 psig) | | | | | | |
| WHSV: 1 | | | | | | |
| Conc. of BTX. Wt. % | 14.3 | 36.9 | 29.6 | 39.4 | 51.7 | 56.2 |
| Prod. Distribution Wt. % | | | | | | |
| C$_1$-C$_3$ | 1.3 | 18.3 | 41.5 | 36.0 | 36.7 | 33.0 |
| C$_4$-C$_9$ (non-aromatics) | 58.0 | 30.2 | 22.6 | 7.4 | 0.5 | 0.2 |
| BZ | 0.2 | 2.6 | 5.0 | 6.3 | 13.1 | 17.9 |
| Toluene | 2.7 | 13.3 | 13.7 | 17.1 | 24.4 | 26.7 |
| Xylenes | 11.4 | 21.0 | 10.9 | 16.0 | 14.2 | 11.6 |
| C$_9$+ Aromatics | 19.6 | 11.1 | 5.3 | 9.9 | 7.0 | 8.0 |
| Durenes | 6.8 | 4.0 | 1.0 | 7.4 | 4.0 | 2.5 |
| Total | 100.0 | 100.0 | 100.0 | 100.0 | 100.0 | 100.0 |

*70/1 SiO$_2$/Al$_2$O$_3$ HZSM-5, containing 0.1 percent by weight of platinum.

What is claimed is:

1. A multistage process for converting lower aliphatic oxygenated hydrocarbon feedstock to hydrocarbon product rich in benzene, toluene and/or xylene which comprises:

contacting said oxygenated hydrocarbons in a primary stage with a medium pore shape selective acidic zeolite to an intermediate hydrocarbon product comprising predominantly aliphatic hydrocarbons;

contacting at least a portion of the aliphatic hydrocarbons from the primary stage with a secondary stage catalyst comprising gallium-promoted medium pore shape selective zeolite characterized by a constraint index within the approximate range of 1 to 12 and a silica to alumina ratio of about 20 to 100:1; thereby producing benzene, toluene, xylene and C$_9$+ aromatic hydrocarbons;

fractionating to recover a C$_9$+ aromatic-rich stream; and recycling said C$_9$+ aromatic stream to the secondary stage for further reaction in contact with the metal-promoted catalyst.

2. The process of claim 1 wherein the metal of said secondary stage catalyst comprises about 0.1 to 1 wt % gallium.

3. The process of claim 1 wherein said primary stage zeolite catalyst comprises ZSM-5 acidic porous crystalline zeolite having a silica to alumina ratio of about 20 to 100:1, and said primary stage is conducted at elevated temperature.

4. The process of claim 1 wherein second stage conversion conditions include a temperature of from about 300° to about 650° C., a pressure of from about $1 \times 10^5$ to about $30. \times 10^5$ pascal and a WHSV of from about 0.1 to about 10.

5. The process of claim 1, 2, 3, or 4 wherein said zeolite of both stages is selected from the group consisting of ZSM-5, ZSM-11, ZSM-12, ZSM-23, ZSM-35, ZSM-38, and ZSM-48.

6. The process of claim 1 wherein the oxygenate feedstock comprises methanol, dimethyl ether or mixtures thereof.

7. The process of claim 1 wherein the second stage aromatics product contains a major amount of C$_6$-C$_8$ aromatic hydrocarbons and a minor amount of C$_9$+ aromatic hydrocarbons.

8. The process of claim 7 wherein said C$_9$+ aromatics are recycled and further converted in the second stage by transalkylation to increase the production of C$_6$-C$_8$ aromatics.

9. In the process for converting oxygenated hydrocarbon feedstock rich in methanol or dimethyl ether in a first stage contacting said feedstock at elevated temperature with an acid medium pore shape selective metallosilicate zeolite catalyst to produce heavier hydrocarbons containing predominantly aliphatics, the improvement which comprises:

further converting at least a portion of the heavier hydrocarbons in a second stage to light aromatics rich in benzene, toluene and/or xylene by contacting said heavier hydrocarbons at elevated temperature with a metal-promoted medium pore shape selective metallosilicate zeolite catalyst under aromatization conditions to produce said light aromatics and a minor amount of $C_9^+$ heavy aromatics;

recovering said $C_9^+$ heavy aromatics for recycle to said second stage;

and further converting said $C_9^+$ heavy aromatics in said second stage in contact with the metal-promoted medium pore shape selective metallosilicate zeolite catalyst to increase $C_6$–$C_8$ light aromatic production.

10. The process of claim 9 wherein said metal-promoted zeolite catalyst comprises a ZSM-5 zeolite having deposited thereon about 0.1 to 1 wt % gallium metal promoter.

* * * * *

UNITED STATES PATENT AND TRADEMARK OFFICE
CERTIFICATE OF CORRECTION

PATENT NO. : 4,686,312

DATED : August 11, 1987

INVENTOR(S) : Yung-Feng Chu et al

It is certified that error appears in the above-identified patent and that said Letters Patent is hereby corrected as shown below:

Title page:

Abstract, line 2, "oxygeanated" should be --oxygenated--
Column 1, line 20, insert space after "$C_6$-$C_8$"
Column 1, line 39, "aliphtic" should be --aliphatic--
Column 1, line 60, "Publsihers" should be -- publishers--
Column 2, line 2, omit space between "conver" and "sion"
Column 2, line 7, insert --be-- after "can"
Column 2, line 9, "produces" should be --produced--
Column 2, line 33, "predominanly" should be --"predominantly--
Column 2, line 36, "righ" should be --rich--
Column 3, line 32, "by" should be --be--
Column 4, line 54, "contracted" should be --contacted--
Column 5, line 42, after "(0 to 200 psig" insert --)--
Column 7, line 30, "4-4" should be --4-5--
Column 8, Claim 9, line 64, insert --by-- after "stage--

Signed and Sealed this

Twenty-third Day of February, 1988

*Attest:*

DONALD J. QUIGG

*Attesting Officer*     *Commissioner of Patents and Trademarks*